United States Patent
Day et al.

(10) Patent No.: US 9,970,815 B2
(45) Date of Patent: May 15, 2018

(54) LIBS ANALYZER SAMPLE PRESENCE DETECTION SYSTEM AND METHOD

(71) Applicant: SciAps, Inc., Woburn, MA (US)

(72) Inventors: David R. Day, Boxford, MA (US); Donald W. Sackett, Bedford, MA (US)

(73) Assignee: SciAps, Inc., Woburn, MA (US)

( * ) Notice: Subject to any disclaimer, the term of this patent is extended or adjusted under 35 U.S.C. 154(b) by 0 days. days.

(21) Appl. No.: 15/484,767

(22) Filed: Apr. 11, 2017

(65) Prior Publication Data
US 2017/0219429 A1    Aug. 3, 2017

Related U.S. Application Data

(60) Division of application No. 14/800,888, filed on Jul. 16, 2015, now Pat. No. 9,651,424, which is a (Continued)

(51) Int. Cl.
*G01J 3/30* (2006.01)
*G01J 3/02* (2006.01)
(Continued)

(52) U.S. Cl.
CPC ............... *G01J 3/027* (2013.01); *G01J 3/10* (2013.01); *G01J 3/443* (2013.01); *G01N 21/718* (2013.01);
(Continued)

(58) Field of Classification Search
CPC ........ G01J 3/02; G01J 3/10; G01J 3/12; G01J 3/027; G01J 3/443; G01J 3/0248;
(Continued)

(56) References Cited

U.S. PATENT DOCUMENTS

| 3,760,144 A | 9/1973 | Herzberger et al. |
| 4,358,659 A | 11/1982 | Spohnheimer |
| (Continued) | | |

FOREIGN PATENT DOCUMENTS

| WO | WO 2012/040769 A1 | 4/2012 |
| WO | WO 2012/135961 A1 | 10/2012 |
| (Continued) | | |

OTHER PUBLICATIONS

Thorlabs, "Off-Axis Parabolic Mirrors With Holes Parallel to Collimated Beam", http://www.thorlabs.us/newgrouppage9.cfm?objectgroup_id=8172, Aug. 13, 2015, 2 pages.
(Continued)

*Primary Examiner* — Jamil Ahmed
(74) *Attorney, Agent, or Firm* — Iandiorio Teska & Coleman, LLP

(57) ABSTRACT

A LIBS analyzer and method includes a laser configured to produce a plasma on a sample at a focal point on the sample and a spectrometer responsive to radiation emitted from the plasma and configured to produce an output spectrum. A detector is positioned to detect low intensity pre-firing radiation produced by the laser and reflected off the sample from the focal point. The intensity of the low intensity pre-firing radiation is compared to a predetermined minimum and the laser pump sequence is halted if the intensity of the low intensity pre-firing radiation is less than the predetermined minimum.

5 Claims, 12 Drawing Sheets

Related U.S. Application Data continuation-in-part of application No. 14/632,419, filed on Feb. 26, 2015, now Pat. No. 9,664,565.

(51) Int. Cl.
   *G01N 21/71* (2006.01)
   *G01J 3/443* (2006.01)
   *G01J 3/10* (2006.01)

(52) U.S. Cl.
   CPC .............. *G01N 2201/069* (2013.01); *G01N 2201/06113* (2013.01)

(58) Field of Classification Search
   CPC .............. G01N 21/71; G01N 21/718; G01N 2201/06113; G01N 2201/069; G01D 5/48; G01D 5/26
   See application file for complete search history.

(56) References Cited

U.S. PATENT DOCUMENTS

| | | |
|---|---|---|
| 4,770,486 A | 9/1988 | Wang et al. |
| 5,473,162 A | 12/1995 | Busch et al. |
| 5,520,679 A | 5/1996 | Lin |
| 6,006,140 A | 12/1999 | Carter |
| 6,077,386 A | 6/2000 | Smith, Jr. et al. |
| 6,355,908 B1 | 3/2002 | Tatah et al. |
| 6,568,418 B1 | 5/2003 | Hope et al. |
| 6,801,595 B2 | 10/2004 | Grodzins et al. |
| 7,233,643 B2 | 6/2007 | Sipilä et al. |
| 7,394,537 B1 | 7/2008 | Lindfors et al. |
| 7,426,019 B2 | 9/2008 | Eklin |
| 7,676,061 B2 | 3/2010 | Harrison et al. |
| 7,821,634 B2 | 10/2010 | Dillon et al. |
| 8,184,287 B2 | 5/2012 | Hamilton et al. |
| 8,199,321 B2 | 6/2012 | Yoo et al. |
| 8,436,991 B2 | 5/2013 | Senac |
| 8,576,382 B2 | 11/2013 | LaValley et al. |
| 8,655,807 B2 | 2/2014 | Multari et al. |
| 9,036,146 B2 | 5/2015 | Day |
| 2001/0015801 A1 | 8/2001 | Hirose et al. |
| 2002/0009814 A1 | 1/2002 | Usui et al. |
| 2002/0174325 A1 | 11/2002 | Iwanaga |
| 2003/0010907 A1 | 1/2003 | Hayek et al. |
| 2003/0234928 A1 | 12/2003 | Lucas et al. |
| 2004/0183010 A1 | 9/2004 | Reilly et al. |
| 2005/0032459 A1 | 2/2005 | Surana et al. |
| 2005/0056628 A1 | 3/2005 | Hu |
| 2005/0068524 A1 | 3/2005 | Wu et al. |
| 2005/0142260 A1 | 6/2005 | Chen et al. |
| 2005/0236563 A1 | 10/2005 | Busch et al. |
| 2005/0248758 A1 | 11/2005 | Carron et al. |
| 2006/0100676 A1 | 5/2006 | Walmsley |
| 2006/0262302 A1 | 11/2006 | Eklin |
| 2007/0187632 A1 | 8/2007 | Igarashi |
| 2007/0195311 A1 | 8/2007 | Morgan et al. |
| 2007/0202613 A1 | 8/2007 | Usul et al. |
| 2007/0265783 A1 | 11/2007 | Mound |
| 2008/0151241 A1 | 6/2008 | Lindfors et al. |
| 2008/0165344 A1 | 7/2008 | Treado et al. |
| 2008/0205755 A1 | 8/2008 | Jackson et al. |
| 2008/0259330 A1 | 10/2008 | Dillon et al. |
| 2009/0007933 A1 | 1/2009 | Thomas et al. |
| 2009/0025761 A1 | 1/2009 | Matsumoto et al. |
| 2009/0057422 A1 | 3/2009 | Dugas et al. |
| 2009/0103082 A1 | 4/2009 | Black et al. |
| 2010/0197116 A1 | 8/2010 | Shah et al. |
| 2011/0100967 A1 | 5/2011 | Yoo et al. |
| 2011/0246145 A1 | 10/2011 | Multari et al. |
| 2011/0315661 A1 | 12/2011 | Morisawa et al. |
| 2012/0029836 A1 | 2/2012 | Hermann |
| 2012/0044488 A1 | 2/2012 | Senac |
| 2012/0085366 A1 | 4/2012 | Hirota |
| 2012/0162642 A1 | 6/2012 | Watson et al. |
| 2012/0206722 A1 | 8/2012 | Grigoropoulos et al. |
| 2012/0236303 A1 | 9/2012 | Marple et al. |
| 2012/0268743 A1 | 10/2012 | Wang et al. |
| 2012/0314214 A1 | 12/2012 | Alexander et al. |
| 2013/0016349 A1 | 1/2013 | Effenberger, Jr. et al. |
| 2013/0271761 A1 | 10/2013 | Rutberg et al. |
| 2013/0342902 A1 | 12/2013 | Krueger et al. |
| 2014/0022531 A1 | 1/2014 | Sackett |
| 2014/0022532 A1 | 1/2014 | Sackett |
| 2014/0125965 A1 | 5/2014 | Nagli et al. |
| 2014/0202490 A1 | 7/2014 | Day |
| 2014/0204375 A1 | 7/2014 | Day |
| 2014/0204376 A1 | 7/2014 | Day |
| 2014/0204377 A1 | 7/2014 | Day et al. |
| 2014/0204378 A1 | 7/2014 | Day |
| 2016/0178434 A1* | 6/2016 | Buckley ............... G01J 3/0248 356/72 |
| 2016/0252398 A1 | 9/2016 | Day |

FOREIGN PATENT DOCUMENTS

| | | | |
|---|---|---|---|
| WO | WO 2013/083950 A1 | 6/2013 | |
| WO | WO 2015/057784 A1 | 4/2015 | |

OTHER PUBLICATIONS

Thorlabs, "Off-Axis Parabolic Mirrors With Holes Parallel to Focused Beam", http://www.thorlab.us/newgrouppage9.cfm?objectgroup_id=7197, Aug. 12, 2015, 3 pages.

Written Opinion of the International Searching Authority for PCT Application No. PCT/US2014/11961 dated May 8, 2014 (six (6) pages).

Written Opinion of the International Searching Authority for PCT Application No. PCT/US2014/11863 dated May 13, 2014 (nine (9) pages).

Written Opinion of the International Searching Authority for PCT Application No. PCT/US2014/16188 dated Feb. 2, 2015 (eight (8) pages).

Written Opinion of the International Searching Authority for PCT Application No. PCT/US2014/12060 dated Jan. 27, 2015 (five (5) pages).

Oxford Instruments, Laser Induced Breakdown Spectroscopy (LIBS), http://www.oxford-instruments.com/products/spectrometers/laser-induced-bre . . . , 2014, (two (2) pages).

Applied Spectra, Inc., Model RT100-EC, http://www.appliedspectra.com/products/rt100-ec.html, 2004-2013, (four (4) pages).

RMG Technology Introduces Hand-Held Laser Analyzer, Recycling Today, http://www.recyclingtoday.com/Article.aspx?article_id=141665, May 29, 2013, (two (2) pages).

Ocean Optics, Laser-Induced Breakdown Spectroscopy, The LIBS2500plus LIBS Systems, http://www/oceanoptics.com/products/libs.asp, 1989-2012, (four (4) pages).

Applied Photonics, LIBSCAN 25, brochure, 1998-2010, (two (2) pages).

European Committee for Electrical Standardization (CENELEC), "Safety of Laser Products—Part 1: Equipment classification requirements", British Standard published under the authority of the Standards Policy and Strategy Committee, Nov. 2007, 3 pages.

CFR—Code of Federal Regulations Title 21, "Title 21—Food and Drugs, Chapter I—Food and Drug Administration, Department of Health and Human Services, Subchapter J—Radiological Health", Revised as of Apr. 1, 2014, 16 pages.

Laser Institute of America, "American National Standard for Safe Use of Lasers", ANSI Z136.1-2007, © 2007, 21 pages.

U.S. Department of Labor "OSHA Technical Manual (OTM)—Section III: Chapter 6", https://www.osha.gov/dts/osta/otm/otm_iii_6.html, efffective date Jan. 20, 1999, 29 pages.

\* cited by examiner

LIBS ANALYZER SAMPLE PRESENCE DETECTION SYSTEM AND METHOD

RELATED APPLICATIONS

This application is a divisional application of U.S. patent application Ser. No. 14/800,888 filed Jul. 16, 2015, which hereby claims the benefit of and priority thereto under 35 U.S.C. § § 119, 120, 363, 365, and 37 C.F.R. § 1.55 and § 1.78, which is incorporated herein by reference, and U.S. patent application Ser. No. 14/800,888 is a continuation-in-part of U.S. patent application Ser. No. 14/632,419 filed Feb. 26, 2015, and claims the benefit of and priority thereto under 35 U.S.C. § § 119, 120, 363, 365, and 37 C.F.R. § 1.55 and § 1.78 which is incorporated herein by this reference. This application is related to U.S. patent application Ser. Nos. 13/746,110 filed Jan. 21, 2013 (U.S. Patent Application Pub. No. 20140204378A1); Ser. No. 13/746,095 filed Jan. 21, 2013 (U.S. Patent Application Pub. No. 20140204375A1); Ser. No. 13/746,108 filed Jan. 21, 2013 (U.S. Patent Application Pub. No. 20140204376A1); Ser. No. 13/746,102 filed Jan. 21, 2013 (U.S. Patent Application Pub. No. 20140202490A1); Ser. No. 14/179,670, filed Feb. 13, 2014 (U.S. Patent Application Pub. No. 20140204377A1) and Ser. No. 14/608,359 filed Jan. 29, 2015 (U.S. Patent Application Pub. No. 20150138545A1), and all are incorporated herein by this reference.

FIELD OF THE INVENTION

The subject invention relates, primarily, in one embodiment, to laser induced breakdown spectroscopy (LIBS).

BACKGROUND OF THE INVENTION

Lasers have been classified according to the potential for causing biological damage. The Laser Institute of America Standard ANSI Z136.1 is used to classify lasers. Government organizations also have standards for the use of lasers. See, for example, 29 C.F.R. 1926.102(b)(2) and 21 C.F.R. 1040. In general, Class I (eye safe) lasers do not emit radiation at known hazard levels. For higher class lasers, eye protection, training, safety protocols, and the like may be required. This is not generally true for Class I lasers.

Those skilled in the art have devised various safety measures for lasers. For example, U.S. Pat. No. 8,576,382, incorporated herein by this reference, discloses the use of a non-eye safe laser (in a LIBS system, for example). The operational range to the intended target is known and if a range unit determines the range to the target while the system is in use is greater than the operational range of the system, the non-eye safe laser is disabled. See also U.S. Pat. No. 7,676,061 incorporated herein by this reference.

In some applications, an eye safe laser for a handheld LIBS analyzer is desired. See U.S. patent application Ser. Nos. 13/746,110 (U.S. Patent Application Pub. No. 20140204378A1) and Ser. No. 14/179,670 (U.S. Patent Application Pub. No. 20140204377A1) by the assignee hereof and incorporated herein by this reference. One reason for incorporating an eye safe laser is to eliminate the regulatory requirements placed on higher class lasers. Still, a higher power (e.g., 6-10 mJ) laser may be needed to detect certain elements in certain samples or targets. A higher power laser may also provide lower detection limits.

SUMMARY OF THE INVENTION

Featured are various embodiments of a LIBS system functioning to detect if a sample is at or proximate the nose of the handheld LIBS analyzer and functionality which prevents further laser shots if the sample is not detected. The result is a safer system. Also featured is a method of insuring any laser shots fired into the air do not adversely affect the spectral analysis of a sample.

Featured is a LIBS analyzer comprising a laser configured to produce a plasma on a sample. a spectrometer responsive to radiation emitted from the plasma, and a controller subsystem configured to control the laser. The controller subsystem is programmed to initiate a laser pump sequence in response to a fire command, analyze radiation to determine if the laser is aimed at a sample and, if the analysis reveals the laser is aimed at the sample, continue pulsing the laser to test the sample for a test duration. If, however, the analysis reveals the laser is not aimed at the sample, the laser pump sequence is halted.

In one version, the analyzed radiation is low intensity pre-firing radiation emitted by the laser (fluorescence emitted by the laser rod during energization or "pumping" that occurs 10's to 100's of microseconds before the laser discharge) and the analyzer further includes a detector positioned to detect the low intensity pre-firing radiation produced by the laser and reflected by the sample. The controller subsystem may be configured to compare the intensity of the detected low intensity pre-firing radiation to a predetermined minimum and halt the laser pump sequence if the detected intensity of the reflected low intensity pre-firing radiation reflected from the sample is less than the predetermined minimum. The controller subsystem may be configured to initiate a laser pump sequence, in response to a fire command, which includes, at least before the first full laser discharge pump duration and a short pump duration which produces the low intensity pre-firing radiation but not a high intensity laser discharge. There may be a short pump duration before each full laser discharge pump duration in the laser pump sequence.

In one example, the detector is located in the spectrometer. In another example the detector is coupled to a fiber of a fiber bundle. In still another example a mirror directs the low intensity pre-firing radiation reflected from the sample to the detector.

In another version, the analyzed radiation is the plasma and the controller subsystem is configured to determine if the laser is aimed at the sample by analyzing an output of the spectrometer. The controller subsystem may be configured to measure the maximum signal output by the spectrometer in a predetermined wavelength range and to automatically halt the laser pump sequence if the maximum signal amplitude in a predetermined wavelength range is less than a predetermined amplitude. In one embodiment, the predetermined amplitude is 200 and the predetermined wavelength range is 200-400 nm.

The controller subsystem is preferably configured to analyze the output of the spectrometer to determine elements present in the sample by averaging spectrum results for each laser pulse. Spectrum results produced by any laser pulse subsequent to a determination that the laser is not aimed at the sample, or that did not produce a plasma (e.g., due to sample porosity) are not used in the averaging algorithm.

Also featured is a LIBS analyzer comprising a laser configured to produce a plasma on a sample at a focal point on the sample, a spectrometer responsive to radiation emitted from the plasma and configured to produce an output, and a detector positioned to detect low intensity pre-firing radiation produced by the laser and reflected off the sample from the focal point. A controller subsystem is responsive to the spectrometer output and to the detector output and is configured to control the laser and to initiate a laser pump sequence in response to a fire command, compare the intensity of the low intensity pre-firing radiation to a predetermined minimum, and halt the laser pump sequence if the intensity of the low intensity pre-firing radiation is less than the predetermined minimum. If the intensity of the low intensity pre-firing radiation is greater than the predetermined minimum, the laser pulse sequence continues. The controller subsystem may be configured to initiate a laser pump sequence, in response to the fire command, which includes, at least before the first full laser discharge pump duration, a short pump duration which produces the low intensity pre-firing radiation but not high intensity laser discharge.

Also featured is a LIBS analysis method comprising firing a laser to produce a plasma on a sample, analyzing radiation to determine if the laser is aimed at a sample, if the analysis reveals the laser is aimed at the sample, continuing firing the laser, and if the analysis reveals the laser is not aimed at the sample, halting the any further laser discharges.

The analyzed radiation may be low intensity pre-firing radiation emitted by the laser. Analyzing radiation to determine if the laser is aimed at the sample may include detecting the low intensity pre-firing radiation reflected by the sample. In another version, analyzing radiation to determine if the laser is aimed at the sample includes analyzing the resulting plasma using a spectrometer producing a spectrum.

One LIBS analysis method includes firing a laser configured to produce a plasma on a sample at a focal point on the sample, and receiving radiation emitted from the plasma and producing a spectrum. Low intensity pre-firing radiation produced by the laser and reflected off the sample is detected and compared to a predetermined minimum. If the intensity of the low intensity pre-firing radiation is less than the predetermined minimum, the laser pump sequence is stopped.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
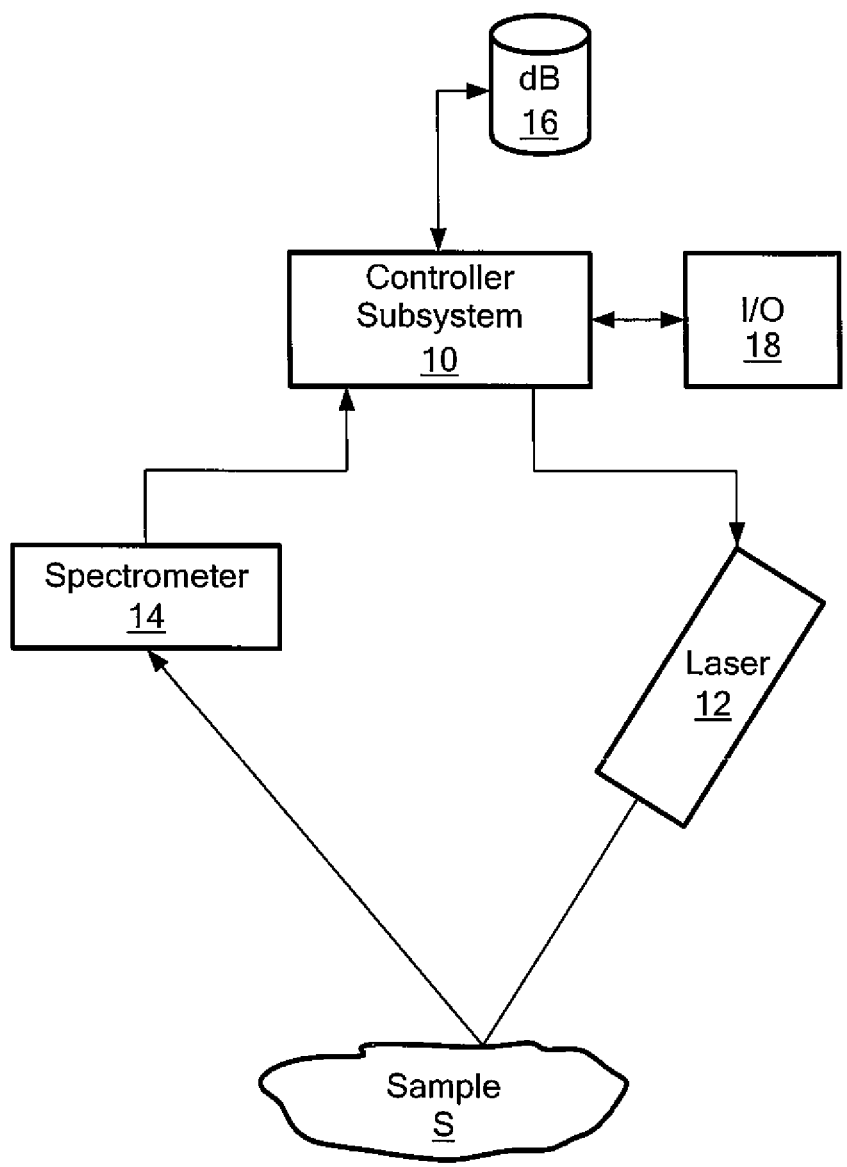
FIG. 1 is a simplified schematic block diagram showing the primary components associated with a LIBS analyzer in accordance with aspects of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows a LIBS system, preferably a handheld analyzer as disclosed in co-pending application U.S. Ser. No. 13/746,110 (U.S. Patent Application Pub. No. 20140204378A1) and Ser. No. 14/179,670 (U.S. Patent Application Pub. No. 20140204377A1) incorporated herein by this reference. Controller subsystem 10 controls the energizing of a diode pumped solid state laser 12 (e.g., 3-10 mJ) to produce a laser beam striking sample S producing a plasma thereon. Typically, the nose section of the handheld LIBS analyzer is designed to be placed directly on sample S. Spectrometer 14 is configured to receive radiation from the resulting plasma and produces a spectrum of wavelength intensities in order to determine the elements and their concentrations present in sample S based, for example, on a spectral library populating database 16 stored in a memory device such as a PROM, EEPROM, flash memory or the like.

Spectrometer 14 may include its own processing capabilities or controller subsystem 10 may include one or more processors programmed to analyze spectral data (from a CCD, for example) produced by one or more spectrometers 14. Different spectrometers may be tailored for different wavelength ranges.

Controller subsystem 10 may include one or more processors as noted above, one or more microcontrollers, applications specific integrated circuits, field programmable gate arrays, or the like carrying out the functions described herein (typically by loading and running computer instructions stored in memory). Input/output section 18 can be used to trigger a firing command (via the push of a trigger or button on the handheld LIBS analyzer, for example). Input/output section 18 typically also includes a display such as a touch screen display for displaying messages, spectral information, test results, and the like.

Figure 2:
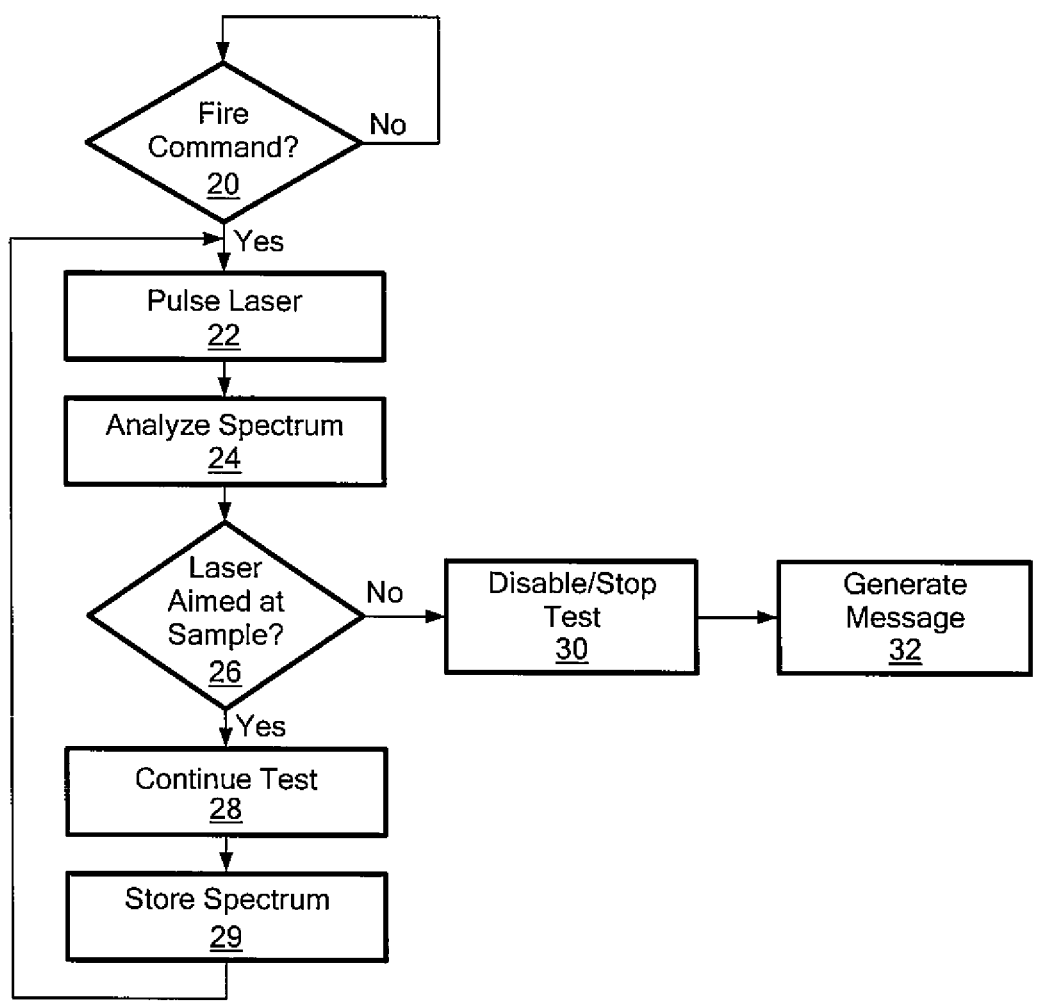
FIG. 2 is a flow chart depicting the primary steps associated with the preferred programming of the controller subsystem of FIG. 1 and also associated with one preferred method of the invention.

Here, controller subsystem 10 is configured (e.g., programmed) to energize laser 12 according to a laser pump sequence to fire the laser, step 22, FIG. 2 when the operator (using input/output section 18) initiates a fire command, step 20 during a test of a sample. After each discharge, the resulting spectrum is analyzed, step 24, FIG. 2 and controller subsystem 10, FIG. 1 is configured to determine whether the laser is aimed at a sample to be analyzed or is instead aimed elsewhere (in air, for example).

Figure 3A:
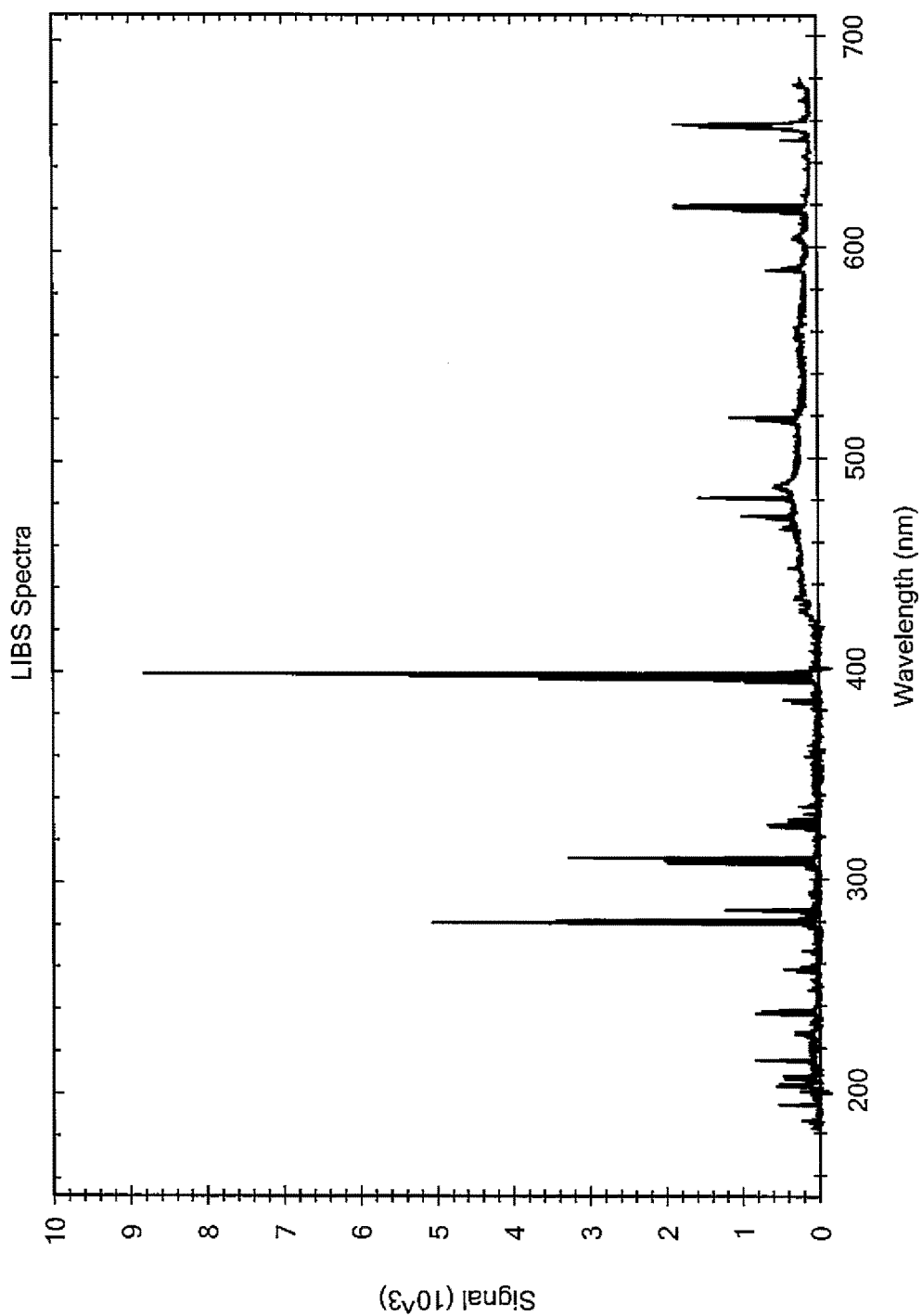
FIGS. 3A-3B are graphs showing a spectrum output by the spectrometer of FIG. 1 when the laser beam strikes a typical sample during a test.
Figure 3B:
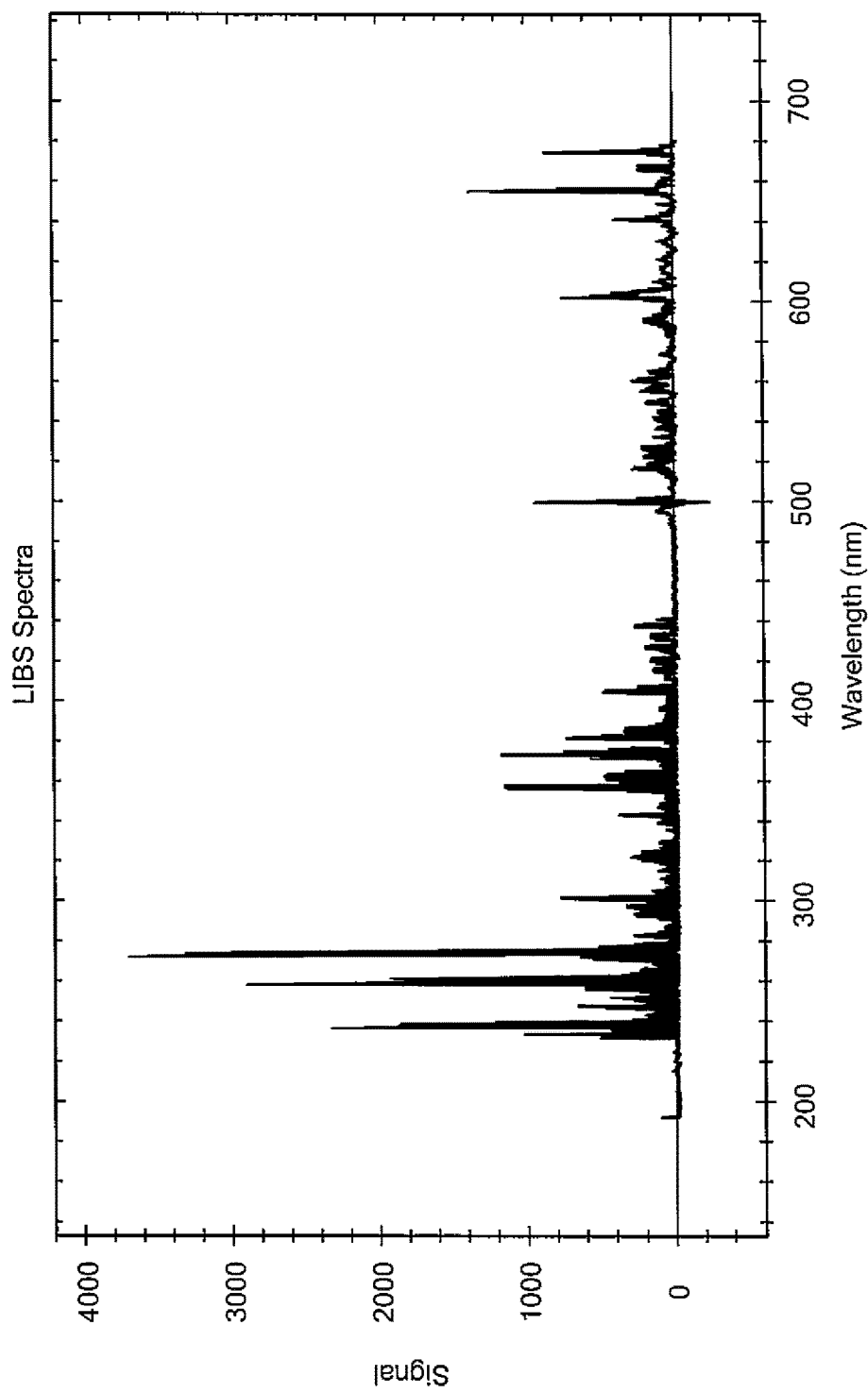

Shown in FIG. 3A is a typical spectrum where the nose section of the LIBS analyzer is placed directly on an aluminum sample and the laser is fired. FIG. 3B shows the spectrum produced for a steel sample. When such a spectrum is output by the spectrometer 14, FIG. 1, controller subsystem 10 automatically continues the test as shown at steps 26 and 28 by continuing to pulse the laser, for example at 10 Hz (or greater) while moving the laser beam about the sample between discharges. Also, between discharges, the spectral dated is stored, step 29. Optional calibration cleaning, and/or autofocus routines may be carried out as well. During the test, the individual spectra are preferably analyzed between laser discharges. Averaging algorithms may be used to determine elemental concentrations based on the collected spectrums.

Figure 4:
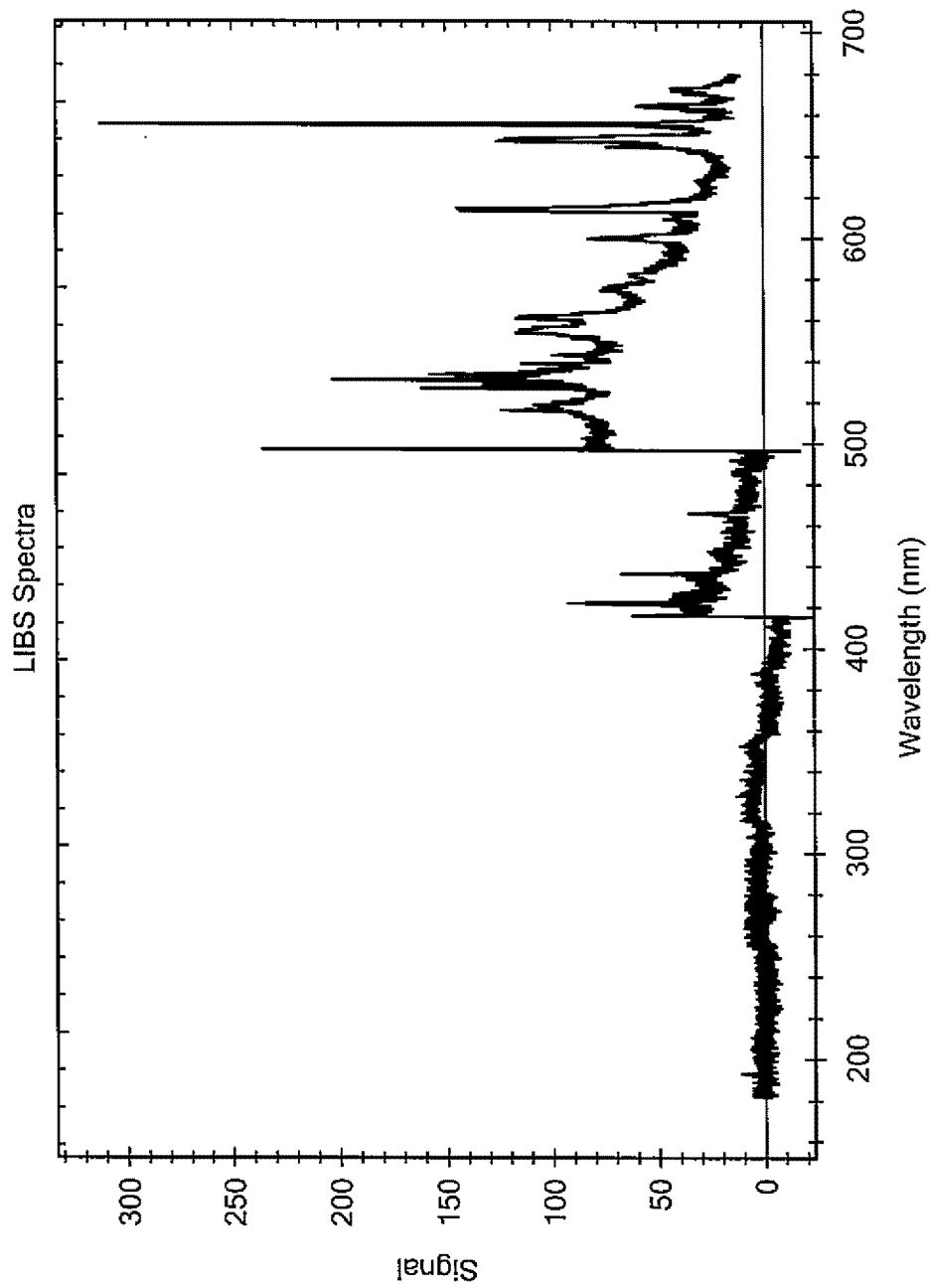
FIG. 4 is a depiction of an example of a spectrum output by the spectrometer of FIG. 1 when the laser beam output by the laser has failed to strike a sample proximate the LIBS analyzer.

If, however, an operator of the handheld LIBS device improperly triggers a fire command when the laser is aimed other than at a proximate sample (possibly even, at another person), then either no plasma will be produced and no spectrum is available for measurement or a plasma is produced in air—the spectrum of which is shown in FIG. 4. Note the highest peak is below 400 and there is no discernable signal at all below about 400 nm. When controller subsystem 10 detects the lack of a wavelength range (e.g., 200-400 nm) or a spectrum as shown in FIG. 4 or close approximations thereof, the laser is disabled and/or the pump sequence is stopped as shown at step 30, FIG. 2 automatically by the controller subsystem. The laser is not further discharged as is the situation with a typical test of a sample. In addition, an error message may be generated by the controller subsystem as shown at step 32 for display on input/output section 18. Also, the "air shot" spectrum of FIG. 4 is not used in the averaging algorithm to more accurately determine elemental concentrations present in the sample based on spectrums collected before the air shot.

In some examples, controller subsystem 10, FIG. 1 searches database 16 for a spectrum matching that shown in FIG. 4, and if a match is found, further firing of the laser is prevented. The spectrums shown in FIG. 4 may be generated during controlled evaluations of the handheld LIBS unit by firing the laser such that the discharged laser beam propagates through the air in a room, for example. Controller subsystem 10 may also reference one or more stored thresholds such that a peak detected below a threshold is indicative of the laser beam being fired through the air and not at a sample located proximate the nose section of the handheld LIBS analyzer.

In one example, the controller is programmed, for each discharge, to measure the maximum signal between a given wavelength range, e.g., between 200 and 400 nm. If the maximum signal there is below a predetermined level, e.g., 200, then the sample is not present (or has been moved relative to the hand held analyzer) and the normal laser pulse train sequence does not continue and the test is stopped.

Thus, if the operator has improperly aimed the laser at something other than a proximate sample to be tested, only one additional pulse of laser energy will be produced. The result is the same if the sample is removed during testing. As such, a higher power laser may be used (e.g., 3-10 mJ) for enhanced LIBS analysis and yet the handheld LIBS analyzer may still be classified as a Class I device. Thus, special training and/or equipment may not be required in order to operate such an analyzer.

According to the ANSI standard, a laser system with an emission duration of $10^{-7}$-$10^{-9}$ seconds at a wavelength of between 1,500-1,800 nm for an 8 mJ laser pulsed once meets the class I standard. Thus, by evaluating whether a sample is present for each pulse, laser 12, FIG. 1 may be an 8 mJ laser emitting at 1534 nm and, provided the emission duration (controlled by controller subsystem 10) is between $10^{-7}$-$10^{-9}$ seconds, the LIBS analyzer of FIG. 1 may be classified as a class I laser. When the sample is present and the pulse train continues during a test, then the emission is blocked by the sample (which essentially serves as an interlock). Accordingly, the ANSI standard for class I lasers may be met with the system shown. A safer system is also realized.

One preferred system is fault tolerant in that controller subsystem 10 includes two processors (e.g., a FPGA and an OMAP processor) processing the spectral data in real time. Assume a LIBS analyzer has a laser with a power P, a wavelength range $\lambda r$, and an emission duration t which meets the class I single pulse ANSI standard. Either processor will stop the laser pump sequence at any time the maximum signal amplitude in an analyzed spectrum over a given wavelength range $\lambda_1$, is less than $A_1$. In one example, P was 8 mJ, $\lambda r$ was 1500-1800, t was $10^{-7}$-$10^{-9}$, $\lambda_1$ was 200-400 nm, and $A_1$ was 200. Note that as shown in FIGS. 3A and 3B typical samples have peaks far greater than 200 in the wavelength range 200-400 nm. If a signal greater than $A_1$ is present in the spectrum in wavelength range $\lambda_1$, the controller subsystem then automatically pulses the laser again. This process continues until the test is complete (typically 10-30 discharges in a typical test duration). If a sample is not present, is moved, if a spectrometer fails, or an optical fiber breaks, or the laser stops firing, the spectrum will not have a signal greater than $A_1$ in the wavelength range $\lambda_1$ and the test will be automatically stopped.

In another example, a diode pumped laser has a wavelength of 1064 nm (at 10 mJ), and an emission duration which meets a class 3 b safety standard. The spectrometer is responsive to radiation emitted by a plasma created by the laser beam and configured to produce a spectrum. The controller subsystem is configured to initiate a laser pump sequence and analyze the resulting spectrum for each laser pulse. The controller halts the laser pump sequence if a maximum signal amplitude in a predetermined wavelength range of the spectrum is less than a predetermined amplitude and continues the laser pump sequence if the maximum signal amplitude in the predetermined wavelength range of the spectrum is greater than the predetermined amplitude. In this example, even though the laser class remains at a 3 b rating, for misuse of the device, at most a single laser pulse can escape the device. Without the pulse spectral monitoring, an operator could fire a large number of laser pulses that miss the sample potentially striking an operator or bystander's eyes.

In FIGS. 1-4, the radiation analyzed to determine if the sample is present proximate the handheld LIBS system is the radiation emitted by the plasma generated on the sample (if present) or in the air (if the sample is not present).

Figure 5:
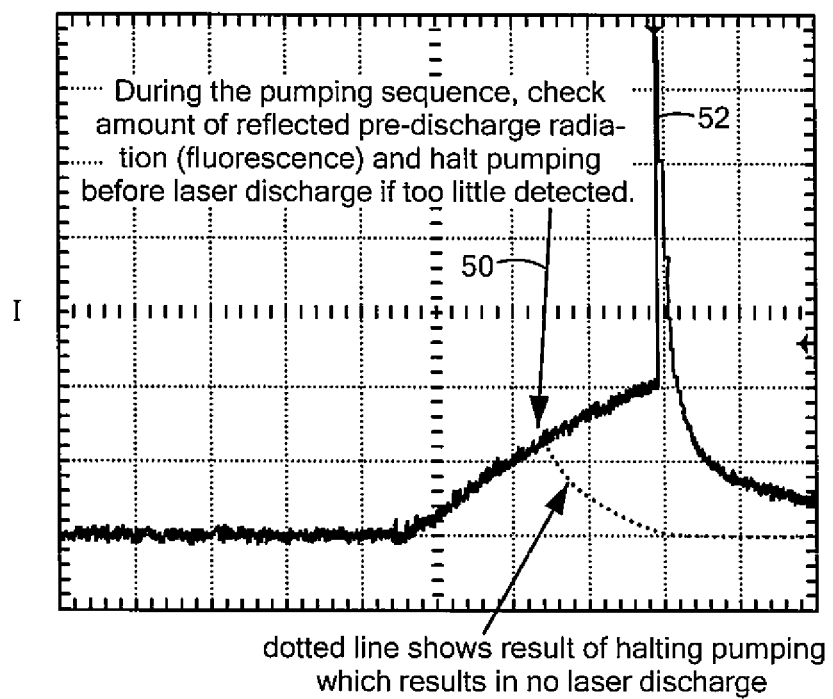
FIG. 5 is a graph of intensity over time for the generation of a high energy laser pulse in a LIBS analyzer diode pumped solid state laser.
Figure 6A:
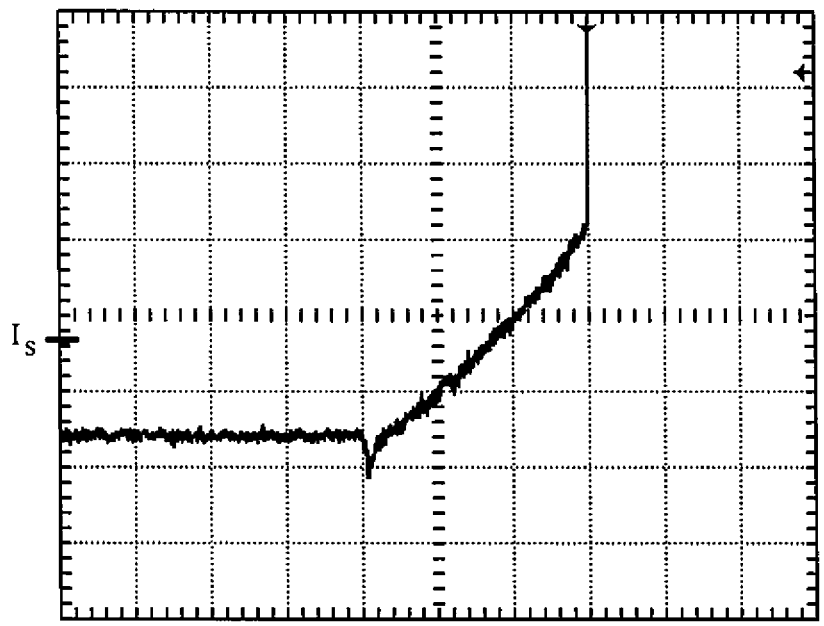
FIGS. 6A-6D are graphs of intensity over time for the low intensity pre-firing radiation relfected off an aluminum sample (FIG. 6A), a steel sample (FIG. 6B), a cardboard sample (FIG. 6C), and the low intensity pre-firing radiation detected when no sample is present (FIG. 6D)
Figure 6B:
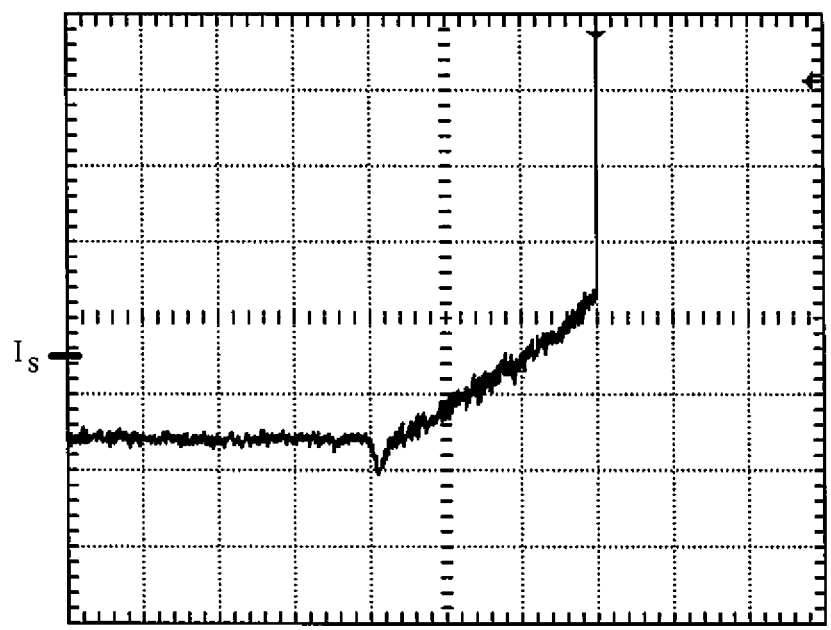
Figure 6C:
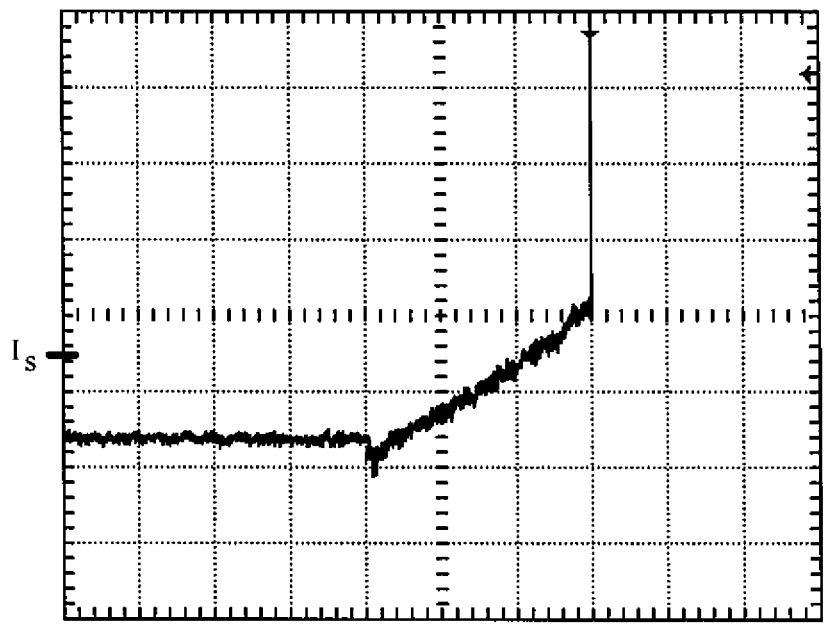
Figure 6D:
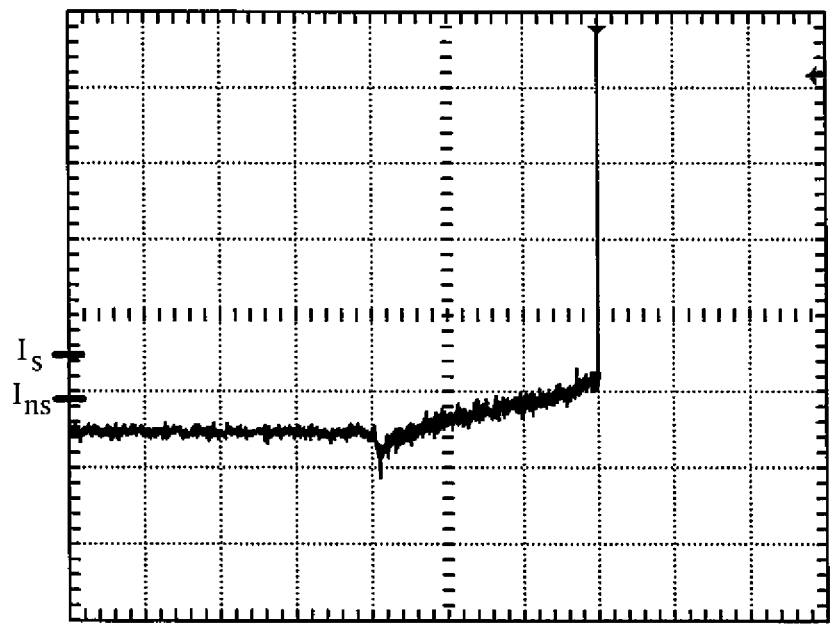

There is another novel method to determine if a sample is present which involves analyzing radiation reflected off the sample. As shown in FIG. 5, when a diode (e.g., 810 nm) pumped solid state laser (1064 nm, 10 mJ) is pumped, low intensity pre-firing radiation (at 1064 nm) (fluorescence) 50 is produced and emitted by the laser before the high intensity laser energy discharge is produced and emitted as shown at 52. When a sample is present at or proximate the nose section of the handheld LIBS analyzer, this low intensity pre-firing radiation is reflected off the sample and can be detected at an intensity level exceeding $I_s$ as shown in FIGS. 6A-6C (Al, steel, and cardboard samples, respectively). But, when a sample is not at or proximate the nose section, then the low intensity pre-firing radiation detected is at or below a intensity $I_s$ as shown in FIG. 6D where the maximum intensity detected is $I_{ns}$. Typically, at 1064 nm, $I_s$ is twice as large as $I_{ns}$ and this difference can be detected, for example, by a photodetector.

So, the method here includes ceasing the laser pumping as shown at time $t_1$ 1) after the low intensity pre-firing radiation is detected and determined to be at an intensity level at or lower than level $I_s$ (or below some preset threshold as determined by testing with samples present and removed) and 2) before the high intensity laser discharge occurs.

Figure 7:
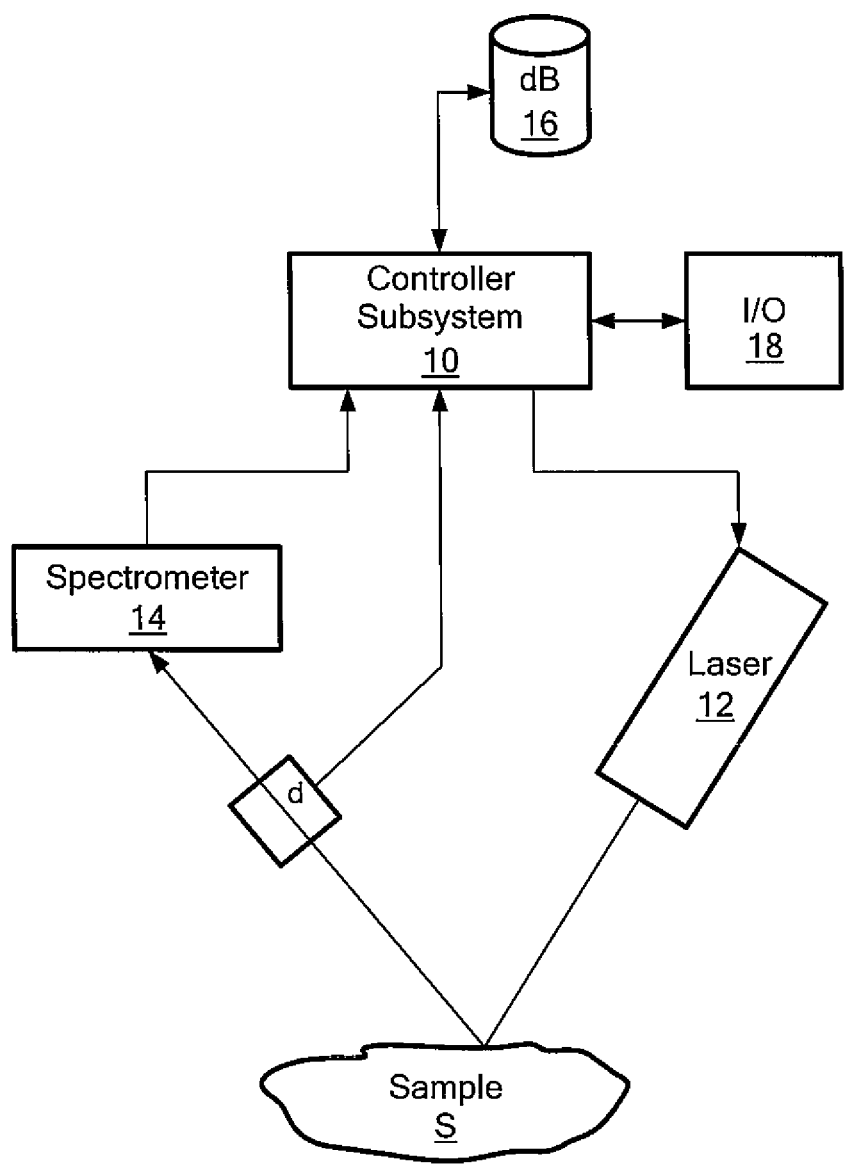
FIG. 7 is a block diagram showing the primary components associated with an embodiment of a LIBS analyzer in accordance with an example of the invention.

As shown in FIG. 7, a detector such as a photodetector (with an optional filter tuned to pass only wavelengths of interest (e.g., 1064)) is included with the LIBS system and positioned to detect the intensity of the low intensity pre-firing radiation produced by laser 12 and reflected by sample S.

Figure 8:
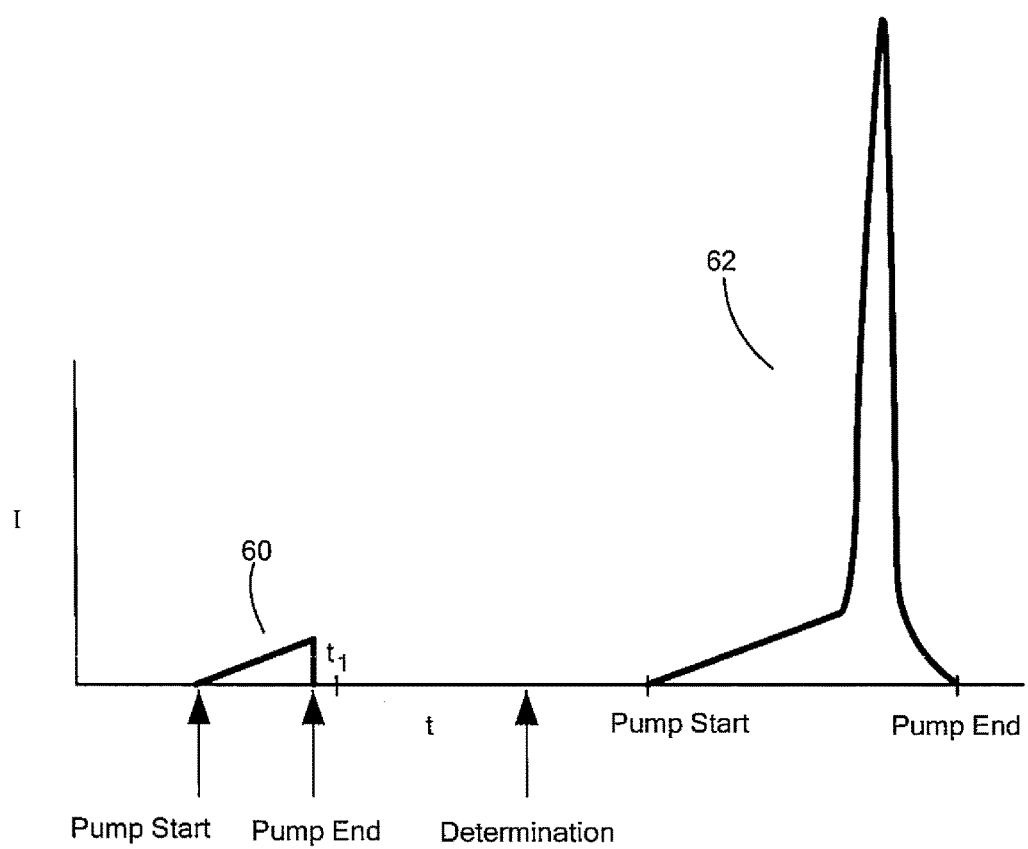
FIG. 8 is a graph of intensity over time for a short pulse sample presence detection method in accordance with an example of the invention.

Detecting this radiation, determining whether the intensity level of the detected radiation is above or below $I_s$, and stopping the diode pumping of the laser gain medium may take too much time, depending on the technology used, to stop the generation of the laser discharge 52, FIG. 5. So, in one embodiment, a short pump duration 60, FIG. 8 is delivered to the laser 12, FIG. 7 under the control of controller subsystem 10 to intentionally produce only low intensity pre-firing radiation the level of which is detected by detector d, FIG. 7 and a decision regarding whether or not the sample is present can be made well before the first full laser discharge pump duration 62, FIG. 8 is generated rendering the decision time much longer (e.g., 100 milliseconds) than the typical time (150 microseconds) between the start and end of the full laser diode pump duration shown at 62 producing the laser discharge.

In some embodiments, there may be a short pump duration 60 before each full laser discharge pump duration in the laser pulse sequence and controller subsystem 10, FIG. 7 is configured to stop the pump sequence any time the analysis of a short pump duration reveals the sample is no longer present proximate the nose of the handheld LIBS device based on the intensity of the low intensity, pre-discharge radiation reflected off the sample. Short pump duration 60, FIG. 8 may be 50 microseconds.

One typical laser pump sequence output by controller subsystem 10, FIG. 7 to laser 12 causes 60 discharges which may take six seconds when firing at 10 hz. But, after element concentration readings are displayed on input/output section 18, a user may be tempted to move the analyzer after a shorter period of time, say three seconds. With the method and technology described above, no laser discharges would be fired in the air thus preventing damage to the eyes of people in the area.

Another scenario addressed by the invention is when a sample, for example, round stock such as a pipe rolls or moves away from the nose of the handheld LIBS analyzer during a laser pump sequence. Again, using the technique described above, no laser discharges are generated after the sample moves to prevent discharges fired into the air.

Figure 9:
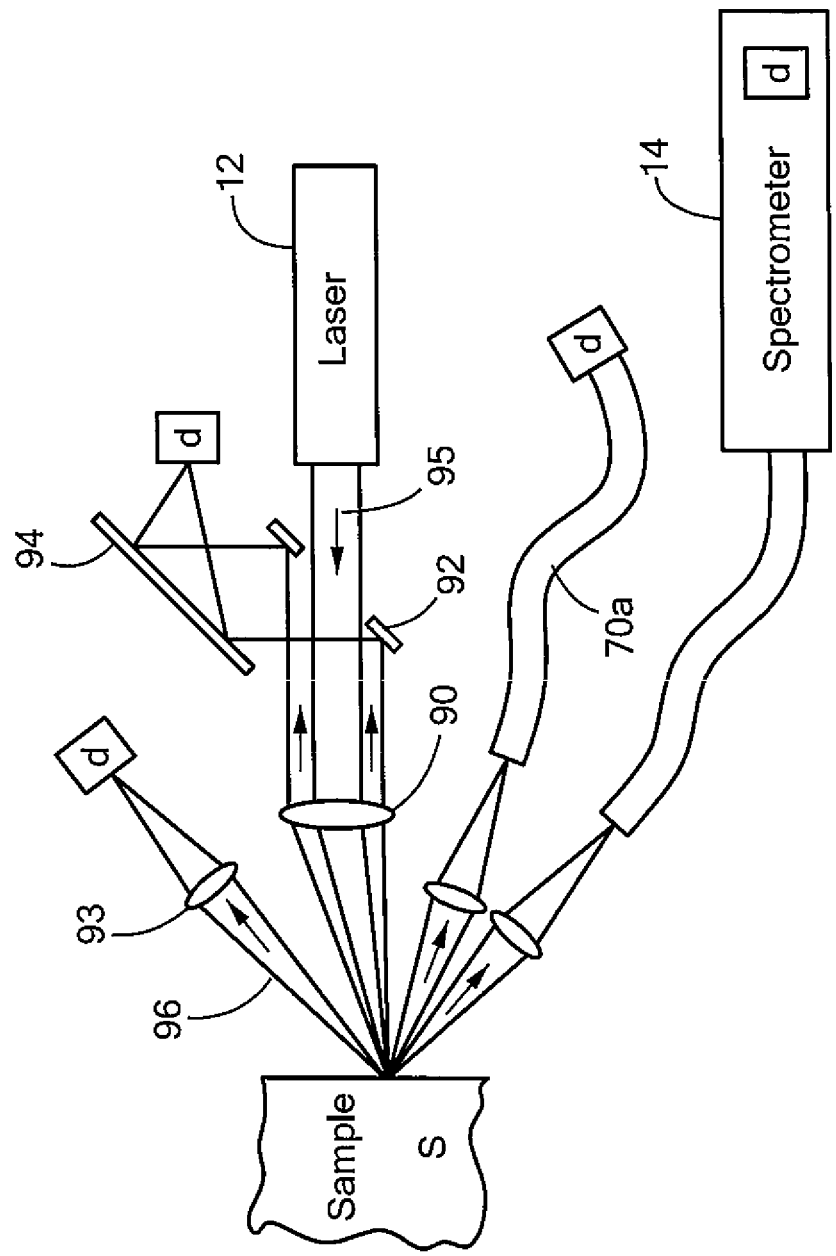
FIG. 9 is a schematic view showing options for where the detector of FIG. 7 can be located.

Detector d, FIG. 9 may be coupled to a fiber 70a, for example a fiber of a fiber bundle in an example where the other fibers are each coupled to a spectrometer. Or, also as shown in FIG. 9, detector d may be within spectrometer 14, for example, attached to the side of mirror inside the spectrometer and arranged to receive radiation reflected off the surface of a sample. See also U.S. patent application Ser. No. 14/608,359 incorporated herein by this reference. In still another exemplary design, detector is positioned such that it receives reflected radiation from sample S through focusing lens 90 after reflecting off mirror 92 and focusing by lens or mirror 94. Mirror 92 has a central opening for passing the laser beam 95 from laser 12. Preferably, the detector is positioned to receive reflected radiation 96 from the focal point of the incident laser radiation on the sample. As also shown in FIG. 9, detector d may receive such radiation as focused onto the detector by lens 93. In another example, the detector is a spectrometer used in the LIBS system.

Between laser discharges, the output of spectrometer 14 (or the output of multiple spectrometers if used) is processed by controller subsystem 10, FIG. 7 to determine and report the concentration of various elements found in a given sample. For any given element, the concentration values determined by multiple laser discharges are typically averaged. If the sample moves or the LIBS analyzer is aimed away from the sample, the spectrometer readings resulting from air shots will be erroneous and it is not desirable that such readings be incorporated into the averaging method.

Thus, in the subject invention, whenever it is determined that any laser discharges were air shots as opposed to laser discharges impinging on and creating a plasma on a sample, the spectrum analysis results for those air shots are ignored, deleted, or otherwise not used in the averaging algorithm. Similarly, if a laser discharge is directed into a pocket of air in a sample, the resulting spectral analysis results are not included in the averaging algorithm. This technique is especially useful for the sample detection technique described above with reference to FIGS. 1-4 where the radiation analyzed in the sample presence detection method is a plasma produced by a high energy laser pulse. Further high energy laser discharges are not generated if it is determined the sample is not present so at most only one high energy laser discharge (air shot) is generated and the spectral analysis of any plasma produced by that discharge is ignored in the averaging algorithm.

For the sample presence detection method described above with reference to FIGS. 5-10 where the radiation analyzed is reflected low intensity pre-firing fluorescence, preferably no high energy laser discharges are produced in air and thus any previously collected data may not need to be adjusted in the averaging algorithm. Still, the data adjustment technique may be useful when still other methods of detecting the presence of a sample are employed to account for any air shots.

Figure 10:
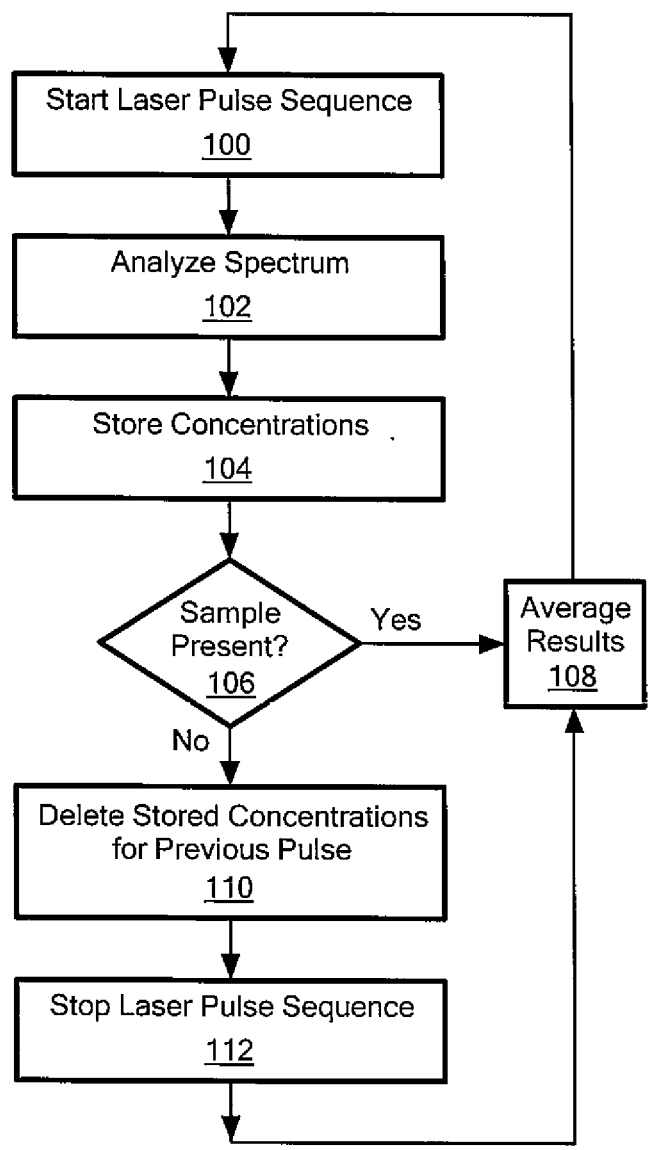
FIG. 10 is flow chart depicting the primary steps associated with the programming of the controller subsystem of FIG. 6 and also associated with a preferred method of the invention.

According, as shown in FIG. 10, controller subsystem 10, FIG. 7 is configured to generate a laser pump sequence and, after each discharge as shown at steps 100 102, the spectrum output by spectrometer subsystem 14, FIG. 7 is analyzed, step 102, FIG. 10. The laser pulse sequence may include one or more short pump durations as shown in FIG. 8. The elemental concentrations calculated by the controller subsystem 10, FIG. 7 may be stored in database 16, step 104, FIG. 10.

One or more sample presence detection algorithms are used as shown at step 106 to determine if a sample is at or proximate the nose section of the handheld LIBS analyzer. If the sample is determined to be present as shown at step 108, all the results of the plurality of laser discharges are averaged. In a scenario, however, where the sample is determined to be absent and a laser discharge is fired into the air as shown at step 106, any stored values for elemental concentrations resulting from the analysis of a spectrum generated by a plasma created by a laser discharge not directed at a sample are deleted or otherwise ignored, step 110 so that the averaging algorithm is not adversely affected by plasmas generated by laser discharges not actually directed at a sample. As shown in step 112, if the sample is determined to not to be present, any further laser discharges are stopped or otherwise not generated by laser 12, FIG. 7 under the control of controller subsystem 10 which interrupts the laser pump sequence. An error or warning message may also be generated.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A LIBS analysis method comprising:
   initiating a laser pump sequence to produce low intensity pre-firing radiation;
   analyzing said low intensity pre-firing radiation to determine if a sample is present;
   if the analysis reveals the sample is present, continuing the laser pump sequence; and
   if the analysis reveals the sample is not present, halting the laser pump sequence.

2. The method of claim 1 in which the intensity of said low intensity pre-firing radiation is compared to a predetermined minimum.

3. The method of claim 1 in which a laser pump sequence includes, at least before the first full laser discharge pump duration, a short pump duration which produces said low intensity pre-firing radiation but not a high intensity laser discharge.

4. The method of claim 3 in which there is a short pump duration before each full laser discharge pump duration in the laser pump sequence.

5. A LIBS analysis method comprising:
   firing a laser configured to produce a plasma on a sample at a focal point on the sample;
   receiving radiation emitted from the plasma and producing a spectrum;
   detecting low intensity pre-firing radiation produced by the laser and reflected off the sample;
   comparing the intensity of said low intensity pre-firing radiation to a predetermined minimum and halting laser firing if the intensity of said low intensity pre-firing radiation is less than said predetermined minimum; and
   continue firing the laser if the intensity of said low intensity pre-firing radiation is greater than said predetermined minimum.

* * * * *